(12) United States Patent
Chen et al.

(10) Patent No.: US 9,138,437 B2
(45) Date of Patent: *Sep. 22, 2015

(54) PYRIMIDINE SUBSTITUTED PURINE COMPOUNDS AS KINASE (S) INHIBITORS

(71) Applicant: VERASTEM, INC., Cambridge, MA (US)

(72) Inventors: DiZhong Chen, Singapore (SG); Meredith Williams, Singapore (SG)

(73) Assignee: Verastem, Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/271,486

(22) Filed: May 7, 2014

(65) Prior Publication Data

US 2015/0105382 A1    Apr. 16, 2015

Related U.S. Application Data

(63) Continuation of application No. 13/262,544, filed as application No. PCT/SG2009/000124 on Apr. 3, 2009, now Pat. No. 8,754,080.

(51) Int. Cl.
*A61K 31/5377* (2006.01)
*C07D 473/32* (2006.01)
*A61P 35/00* (2006.01)

(52) U.S. Cl.
CPC .......... *A61K 31/5377* (2013.01); *C07D 473/32* (2013.01)

(58) Field of Classification Search
CPC ......................... C07D 473/32; A61K 31/5377
USPC ...................... 514/234.2, 234.5; 544/117, 118
See application file for complete search history.

(56) References Cited

U.S. PATENT DOCUMENTS

| | | | |
|---|---|---|---|
| 4,617,304 A | 10/1986 | Ashton et al. | |
| 4,772,606 A | 9/1988 | Sircar et al. | |
| 8,247,410 B2 | 8/2012 | Nagaraj et al. | |
| 8,609,838 B2 | 12/2013 | Nagaraj et al. | |
| 8,754,080 B2 * | 6/2014 | Chen et al. | 514/234.2 |
| 2007/0142402 A1 | 6/2007 | Ding et al. | |
| 2009/0318411 A1 | 12/2009 | Castanedo et al. | |
| 2010/0298319 A1 | 11/2010 | Nagaraj et al. | |
| 2011/0009403 A1 | 1/2011 | Nagaraj et al. | |
| 2011/0105500 A1 | 5/2011 | Nagaraj et al. | |
| 2014/0066620 A1 | 3/2014 | Mysore et al. | |

FOREIGN PATENT DOCUMENTS

| | | |
|---|---|---|
| CN | 101296928 A | 10/2008 |
| EP | 1277738 A1 | 1/2003 |
| GB | 2431156 A | 4/2007 |
| JP | H06049033 A | 2/1994 |
| JP | 2005120102 A | 5/2005 |
| JP | 2006514118 A | 4/2006 |
| WO | 9901454 A1 | 1/1999 |
| WO | 02055521 A1 | 7/2002 |
| WO | 03031406 A2 | 4/2003 |
| WO | 2004016612 A2 | 2/2004 |
| WO | 2004021979 A2 | 3/2004 |
| WO | 2004035740 A2 | 4/2004 |
| WO | 2004037823 A1 | 5/2004 |
| WO | 2004048365 A1 | 6/2004 |
| WO | 2007021937 A2 | 2/2007 |
| WO | 2007031726 A1 | 3/2007 |
| WO | 2007034185 A1 | 3/2007 |
| WO | 2008043031 A1 | 4/2008 |
| WO | 2008090181 A1 | 7/2008 |
| WO | 2008116129 A2 | 9/2008 |
| WO | 2009099163 A1 | 8/2009 |
| WO | 2009157880 A1 | 12/2009 |
| WO | 2010005558 A2 | 1/2010 |
| WO | 2010114484 A1 | 10/2010 |
| WO | 2010114494 A1 | 10/2010 |

OTHER PUBLICATIONS

International Preliminary Report on Patentability & Written Opinion for PCT/SG2009/00124 dated Apr. 10, 2011.
International Report on Patentability for PCTSG2008000379 dated Apr. 7, 2010.
International Search Report for PCT/SG2009/000124 dated Oct. 28, 2009.
International Search Report for PCTSG2008000379 dated Apr. 9, 2009.
Still et al, "Rapid chromatographic technique for preparative separations with moderate resolution" J. Org. Chem., 2923 (1978).
Written Opinion for PCTSG2008000379 dated Apr. 5, 2010.

* cited by examiner

*Primary Examiner* — Sreeni Padmanabhan
*Assistant Examiner* — Irina Neagu
(74) *Attorney, Agent, or Firm* — Lando & Anastasi, LLP

(57) ABSTRACT

The present invention relates to a purine compound useful as a kinase inhibitor. The compound has the structure:

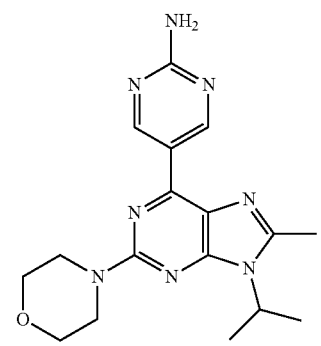

or a pharmaceutically acceptable salt thereof.

6 Claims, No Drawings

PYRIMIDINE SUBSTITUTED PURINE COMPOUNDS AS KINASE (S) INHIBITORS

The instant application, filed on 7 May 2014, is a continuation of U.S. patent application Ser. No. 13/262,544, filed on 27 Dec. 2011, which is a National Stage entry of International Patent Application PCT/SG2009/000124, filed 3 Apr. 2009.

FIELD

The present invention relates to 5-(9-isopropyl-8-methyl-2-morpholin-4-yl-9H-purin-6-yl)-pyrimidin-2-ylamine, methods for its preparation, pharmaceutical compositions containing this compound and uses of this compound in the treatment of certain kinase related disorders/conditions.

BACKGROUND

The search for kinase inhibitors has proven to be a fruitful area for the development of useful pharmaceutically active substances. Kinases, which are alternatively known as phosphotransferases, are enzymes that transfer phosphate groups from high energy donor molecules (for example ATP) to specific target molecules (typically called substrates) in a process termed phosphorylation. One of the largest groups of kinases are the protein kinases which act on and modify the activity of specific proteins.

As a result of the potential of kinase inhibitors to act as pharmaceutically active compounds a significant amount of research has been carried out to discover compounds that display appropriate activity against these targets. In the cancer area two kinases that have attracted attention as potential targets for therapeutic compounds include mTOR and PI3. An example of research in this area is that disclosed in PCT/SG2008/000379 which discloses a number of compounds having kinase activity against both mTOR and PI3.

Compounds that inhibit both mTOR and PI3 kinases simultaneously may be expected to provide powerful antiproliferative, anti-angiogenic and antitumor activity since these compounds act at multiple points in the PI3K/Akt/mTOR pathway. A number of inhibitors of this type are now being investigated in a clinical setting for the first time (e.g. BEZ235, XL765, GDC0941, PX866, SF1126).

In the search for suitable drug candidates a number of factors are taken into consideration in the final determination of whether a compound is a suitable drug candidate or not. Accordingly in making an assessment of a potential compound for further development a number of factors are taken into consideration in addition to the primary inhibitory activity of the compound per se. In making this assessment the skilled medicinal chemist looks at the "drug like properties" of the molecule and includes an assessment of factors such as its activity against the target of interest, the solubility of the compounds of interest (if they are not soluble they typically make poor drug candidates), the metabolic stability of the compound in vitro and in vivo, and the potential side effects that could be caused by the compound on the body amongst others. The present applicants have identified a compound with significantly improved drug like properties in comparison with other compounds in the area.

SUMMARY

The present invention provides a compound of the formula (I):

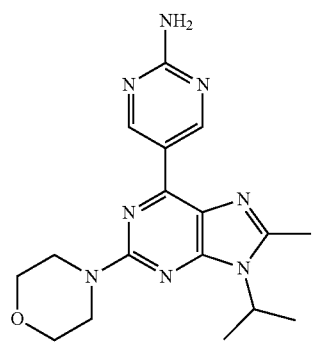 [SMILES: Cc1nc2c(-c3cnc(N)nc3)nc(N3CCOCC3)nc2n1C(C)C]

Formula (I)

or a pharmaceutically acceptable salt thereof.

In addition to the compound of Formula I, the embodiments disclosed are also directed to pharmaceutically acceptable salts, pharmaceutically acceptable N-oxides, pharmaceutically acceptable prodrugs, and pharmaceutically active metabolites of the compound, and pharmaceutically acceptable salts of such metabolites.

The invention also relates to pharmaceutical compositions including the compound of the invention with a pharmaceutically acceptable carrier, diluent or excipient.

In a further aspect the invention provides a method of inhibiting a protein kinase selected from the group consisting of a serine/threonine protein kinase or a fragment or a complex thereof or a functional equivalent thereof and a PI3 kinase or a fragment or a complex thereof or a functional equivalent thereof, the method including exposing the protein kinase or a fragment or complex thereof or a functional equivalent thereof and/or co-factor(s) thereof to an effective amount of a compound of the invention.

The compound disclosed herein may act directly and solely on the kinase molecule or a complex or fragment thereof to inhibit biological activity. However, it is understood that the compound may also act at least partially on co-factors that are involved in the phosphorylation process. Known kinase co-factors include ionic species (such as zinc and calcium), lipids (such as phosphatidylserine), and diacylglycerols.

In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof. In some embodiments the serine/threonine protein kinase is mTORC2 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In one embodiment of the method exposing the one or more protein kinase(s) to the compound includes administering the compound to a mammal containing the one or more protein kinase(s).

In an even further aspect the invention provides the use of a compound of the invention to inhibit one or more protein kinase(s) selected from the group consisting of a serine/threonine protein kinase or a fragment or a complex thereof or a functional equivalent thereof and a PI3 kinase or a fragment or a complex thereof or a functional equivalent thereof.

In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof. In some embodiments the serine/threonine protein kinase is mTORC2 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In an even further aspect the invention provides a method of treating or preventing a condition in a mammal in which inhibition of one or more protein kinase(s) selected from the group consisting of a serine/threonine protein kinase or a fragment or a complex thereof or a functional equivalent thereof and a PI3 kinase or a fragment or a complex thereof or a functional equivalent thereof, prevents, inhibits or ameliorates a pathology or a symptomology of the condition, the method including administration of a therapeutically effective amount of a compound of the invention.

In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof. In some embodiments the serine/threonine protein kinase is mTORC2 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In some embodiments the condition is cancer. In some embodiments the cancer is selected from the group consisting of Hematologic cancer such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, acute T-cell leukemia, myelodysplastic syndromes, plasma cell disorder, hairy cell leukemia, kaposi's sarcoma, lymphoma and hyperproliferative conditions such as psoriasis and restenosis; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculo-skeleton diseases such as osteosarcoma, musculoskeleletal neoplasm; Squamous cell carcinoma and fibroid tumour. In other embodiments, the compound of this invention can be used to treat pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

In some embodiments the condition is an autoimmune or inflammatory disease or a disease supported by excessive neovascularisation. Diseases that have been attributed with some degree of autoimmune etiology, or that involve pathological inflammatory and neovascularization responses, include the following: acute disseminated encephalomyelitis, Addison's disease, agammaglobulinemia, agranulocytosis, allergic asthma, allergic encephalomyelitis, allergic rhinitis, alopecia areata, alopecia senilis, anerythroplasia, ankylosing spondylitis, antiphospholipid antibody syndrome, aortitis syndrome, aplastic anemia, atopic dermatitis, autoimmune haemolytic anemia, autoimmune hepatitis, autoimmune oophoritis, Balo disease, Basedow's disease, Behcet's disease, bronchial asthma, Castleman's syndrome, celiac disease, Chagas disease, chronic inflammatory demyelinating polyneuropathy, Churg-Strauss syndrome, Cogans syndrome, cornical cornea, comical leukoma, Coxsackie myocarditis, CREST disease, Crohn's disease, cutaneous eosinophilia, cutaneous T-cell lymphoma, dermatitis erythrema multiforme, dermatomyositis, diabetic retinopathy, Dressler's syndrome, dystrophia epithelialis corneae, eczematous dermatitis, endometriosis, eosinophilic fasciitis, eosinophilic gastroenteritis, epidermolysis bullosa, Evans syndrome, fibrosing alveolitis, gestational pemphigoid, glomerulonephritis, Goodpasture's syndrome, graft-versus-host disease, Graves' disease, Guillain-Barre Syndrome, Hashimoto's disease, haemolytic-uretic syndrome, herpetic keratitis, ichthyosis vulgaris, idiopathic intersititial pneumonia, idiopathic thrombocytopenic purpura, inflammatory bowel diseases, Kawasaki's disease, keratitis, keratoconjunctivitis, Lambert-Eaton syndrome, leukoderma vulgaris, lichen planus, lichen sclerosus, Lyme disease, linear IgA disease, macular degeneration, megaloblastic anemia, Meniere's disease, Mooren's ulcer, Mucha-Habermann disease, multiple myositis, multiple sclerosis, myasthenia gravis, necrotizing enterocolitis, neuromyelitis optica, ocular pemphigus, opsoclonus myoclonus syndrome, Ord's thyroiditis, paroxysmal nocturnal hemoglobinuria, Parsonnage-Turner syndrome, pemphigus, periodontitis, pernicious anemia, pollen allergies, polyglandular autoimmune syndrome, posterior uveitis, primary biliary cirrhosis, proctitis, pseudomembranous colitis, psoriasis, pulmonary emphysema, pyoderma, Reiter's syndrome, reversible obstructive airway disease, rheumatic fever, rheumatoid arthritis, sarcoidosis, scleritis, Sezary's syndrome, Sjogren's syndrome, subacute bacterial endocarditis, systemic lupus erythematosus, Takayasu's arteritis, temporal arteritis, Tolosa-Hunt syndrome, Type I diabetes mellitus, ulcerative colitis, urticaria, vernal conjunctivitis, vitiligo, Vogy-Koyanagi-Harada syndrome and Wegener's granulomatosis. In some embodiments the condition is endometriosis.

In an even further aspect the invention provides use of a compound of the invention in the preparation of a medicament for treating a condition in an animal in which inhibition of one or more protein kinase(s) selected from the group consisting of a serine/threonine protein kinase or a fragment or a complex thereof or a functional equivalent thereof and a PI3 kinase or a fragment or a complex thereof or a functional equivalent thereof, prevents, inhibits or ameliorates a pathology or a symptomology of the condition.

In another aspect the present invention provides the use of a compound of the invention or a pharmaceutically acceptable salt, N-oxide or prodrug thereof in the treatment of a condition in which inhibition of one or more protein kinase(s) selected from the group consisting of a serine/threonine protein kinase or a fragment or a complex thereof or a functional equivalent thereof and a PI3 kinase or a fragment or a complex thereof or a functional equivalent thereof, prevents, inhibits or ameliorates a pathology or a symptomology of the condition In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof. In some embodiments the serine/threonine protein kinase is mTORC2 or a fragment or complex thereof or a functional equivalent thereof.

In some embodiments the protein kinase is a PI3 kinase or a fragment thereof or a complex thereof or a functional equivalent thereof. In some embodiments the PI3 kinase or a fragment thereof or a complex thereof or a functional equivalent thereof, is a class I PI3K or a fragment thereof or a complex thereof or a functional equivalent thereof.

In another aspect the present invention provides a method of prevention or treatment of a proliferative condition in a subject, the method including administration of a therapeutically effective amount of a compound of the invention.

In another aspect the present invention provides the use of a compound of the invention in the preparation of a medicament for treating a proliferative condition in a subject.

In some embodiments the condition is cancer. In some embodiments the cancer is selected from the group consisting of Hematologic cancer such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, acute T-cell leukemia, myelodysplastic syndromes, plasma cell disorder, hairy cell leukemia, kaposi's sarcoma, lymphoma; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculo-skeleton diseases such as osteosarcoma, musculoskeleletal neoplasm; Squamous cell carcinoma and fibroid tumour. In some embodiments the condition is endometriosis.

Additionally, Formula (I) is intended to cover, where applicable, solvated as well as unsolvated forms of the compound. Thus, each formula includes compounds having the indicated structure, including the hydrated as well as the non-hydrated forms.

These and other features of the present teachings are set forth herein.

DETAILED DESCRIPTION

In this specification a number of terms are used which are well known to a skilled addressee. Nevertheless for the purposes of clarity a number of terms will be defined.

The term "pharmaceutically acceptable salts" refers to salts that retain the desired biological activity of the above-identified compound, and include pharmaceutically acceptable acid addition salts and base addition salts. Suitable pharmaceutically acceptable acid addition salts of compound of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compound, agents and salts may exist in different crystalline or polymorphic forms, all of which are intended to be within the scope of the present invention and specified formulae.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "functional equivalent" is intended to include variants of the specific protein kinase species described herein. It will be understood that kinases may have isoforms, such that while the primary, secondary, tertiary or quaternary structure of a given kinase isoform is different to the prototypical kinase, the molecule maintains biological activity as a protein kinase. Isoforms may arise from normal allelic variation within a population and include mutations such as amino acid substitution, deletion, addition, truncation, or duplication. Also included within the term "functional equivalent" are variants generated at the level of transcription. Other functional equivalents include kinases having altered post-translational modification such as glycosylation.

The compound of the invention displays superior drug like properties which are described in greater detail below, in comparison to structurally similar compounds in the area. These superior properties suggest that the compound of the invention may well be the compound of choice as a pharmaceutical development candidate in the area. As a first observation the compound of the invention displays comparable if not superior activity in the inhibition of the two kinases of interest namely mTOR and PI3. The activity of the compound of the invention against PI3 is stronger than all comparator compounds tested and it displays activity against mTOR that is both comparable to comparator compounds as well as being at an acceptable level for therapeutic applications.

Notwithstanding that the enzyme activity tests indicate that almost all comparator compounds had acceptable activity levels the further testing of the compounds indicated that a number could be ruled out as pharmaceutical development candidates on other grounds. Thus for example the compound of the invention had a reasonable aqueous solubility level (178 μM) indicating that it can be formulated into an orally absorbable pharmaceutical formulation whereas a number of the comparator compounds did not demonstrate acceptable solubility. As such the compound of the invention displayed the combination of excellent activity and acceptable solubility characteristics.

Of the compounds that displayed the combination of activity and solubility the compound of the invention was far superior in its metabolic stability properties. The compound of the invention had excellent stability in human liver microsome studies indicating that it was robust and relatively resistant to degradation in the physiological environment. In contrast the other compounds that displayed the combination of activity and solubility were nowhere near as stable in these studies. As such the compound of the present invention demonstrates a unique combination of activity, solubility and stability that make it superior as a drug candidate in comparison to related compounds in the area notwithstanding the apparent close structural similarity of some of these compounds.

The compound of the invention has the ability to inhibit the activity of certain protein kinases. The ability to inhibit kinase activity may be a result of the compound of the invention acting directly and solely on the kinase molecule to inhibit biological activity. However, it is understood that the compound may also act at least partially on co-factors of the kinase in question that are involved in the phosphorylation process. The compound may have activity against PI3 protein kinases or a fragment or a complex or a functional equivalent thereof. The compound may have activity against certain serine/threonine kinases such as mTOR or a fragment or complex or functional equivalent thereof.

The inhibition of the protein kinase may be carried out in any of a number of well known ways in the art. For example if inhibition of the protein kinase in vitro is desired an appropriate amount of the compound of the invention may be added to a solution containing the purified kinase enzyme. In circumstances where it is desired to inhibit the activity of the kinase in a mammal the inhibition of the kinase typically involves administering the compound to a mammal containing the kinase.

Accordingly the compound of the invention may find a multiple number of applications in which their ability to inhibit protein kinases of the type mentioned above can be utilised. For example the compounds may be used to inhibit serine/threonine protein kinases. The compounds may also be used in treating or preventing a condition in a mammal in which inhibition of a protein kinase and/or co-factor thereof prevents, inhibits or ameliorates a pathology or a symptomology of the condition.

The compound disclosed has the ability to be used in the treatment of proliferative disorders. An example of such a disorder is cancer. It is anticipated that the compounds will have the ability to treat both solid and liquid tumors. In some embodiments the cancers that may be treated by a compound of the present invention include solid tumors and hematological cancers.

As used herein, the term "cancer" is a general term intended to encompass the vast number of conditions that are characterized by uncontrolled abnormal growth of cells. It is anticipated that the compounds of the invention will be useful in treating various cancers including but not limited to bone cancers, brain and CNS tumours, breast cancers, colorectal cancers, endocrine cancers including adrenocortical carcinoma, pancreatic cancer, pituitary cancer, thyroid cancer, parathyroid cancer, thymus cancer, gastrointestinal cancers, Liver cancer, extra hepatic bile duct cancer, gastrointestinal carcinoid tumour, gall bladder cancer, genitourinary cancers, gynaecological cancers, head and neck cancers, leukemias, myelomas, hematological disorders, lung cancers, lymphomas, eye cancers, skin cancers, soft tissue sarcomas, adult soft tissue sarcoma, Kaposi's sarcoma, urinary system cancers.

Exemplary cancers that may be treated by compounds of this invention include Hematologic cancer such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, acute T-cell leukemia, myelodysplastic syndromes, plasma cell disorder, hairy cell leukemia, kaposi's sarcoma, lymphoma and hyperproliferative conditions such as psoriasis and restenosis; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculo-skeleton diseases such as osteosarcoma, musculoskeleletal neoplasm; Squamous cell carcinoma and fibroid tumour. Compounds of this invention may also be used to treat pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

It is also anticipated that the compound of the invention will be useful in treating autoimmune or inflammatory diseases or diseases supported by excessive neovascularisation. Diseases that have been attributed with some degree of autoimmune etiology, or that involve pathological inflammatory and neovascularization responses, include, but are not limited to, the following: acute disseminated encephalomyelitis, Addison's disease, agammaglobulinemia, agranulocytosis, allergic asthma, allergic encephalomyelitis, allergic rhinitis, alopecia areata, alopecia senilis, anerythroplasia, ankylosing spondylitis, antiphospholipid antibody syndrome, aortitis syndrome, aplastic anemia, atopic dermatitis, autoimmune haemolytic anemia, autoimmune hepatitis, autoimmune oophoritis, Balo disease, Basedow's disease, Behcet's disease, bronchial asthma, Castleman's syndrome, celiac disease, Chagas disease, chronic inflammatory demyelinating polyneuropathy, Churg-Strauss syndrome, Cogans syndrome, cornical cornea, cornical leukoma, Coxsackie myocarditis, CREST disease, Crohn's disease, cutaneous eosinophilia, cutaneous T-cell lymphoma, dermatitis erythrema multiforme, dermatomyositis, diabetic retinopathy, Dressler's syndrome, dystrophia epithelialis corneae, eczematous dermatitis, eosinophilic fasciitis, eosinophilic gastroenteritis, epidermolysis bullosa, Evans syndrome, fibrosing alveolitis, gestational pemphigoid, glomerulonephritis, Goodpasture's syndrome, graft-versus-host disease, Graves' disease, Guillain-Barre Syndrome, Hashimoto's disease, haemolytic-uretic syndrome, herpetic keratitis, ichthyosis vulgaris, idiopathic intersititial pneumonia, idiopathic thrombocytopenic purpura, inflammatory bowel diseases, Kawasaki's disease, keratitis, keratoconjunctivitis, Lambert-Eaton syndrome, leukoderma vulgaris, lichen planus, lichen sclerosus, Lyme disease, linear IgA disease, macular degeneration, megaloblastic anemia, Meniere's disease, Mooren's ulcer, Mucha-Habermann disease, multiple myositis, multiple sclerosis, myasthenia gravis, necrotizing enterocolitis, neuromyelitis optica, ocular pemphigus, opsoclonus myoclonus syndrome, Ord's thyroiditis, paroxysmal nocturnal hemoglobinuria, Parsonnage-Turner syndrome, pemphigus, periodontitis, pernicious anemia, pollen allergies, polyglandular autoimmune syndrome, posterior uveitis, primary biliary cirrhosis, proctitis, pseudomembranous colitis, psoriasis, pulmonary emphysema, pyoderma, Reiter's syndrome, reversible obstructive airway disease, rheumatic fever, rheumatoid arthritis, sarcoidosis, scleritis, Sezary's syndrome, Sjogren's syndrome, subacute bacterial endocarditis, systemic lupus erythematosus, Takayasu's arteritis, temporal arteritis, Tolosa-Hunt syndrome, Type I diabetes mellitus, ulcerative colitis, urticaria, vernal conjunctivitis, vitiligo, Vogy-Koyanagi-Harada syndrome and Wegener's granulomatosis. In some embodiments the condition is endometriosis.

The compound of the invention may also be used the preparation of a medicament for treating a condition in an animal in which inhibition of a protein kinase can prevent, inhibit or ameliorate the pathology or symptomology of the condition. The compound of the invention may also be used in the preparation of a medicament for the treatment or prevention of a kinase-related disorder.

Administration of the compound of Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the inhibitor compound may be selectively toxic or more toxic to rapidly proliferating cells, e.g. cancerous tumours, than to normal cells.

In using the compound of the invention it can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compound of the present invention can be administered alone or in the form of a pharmaceutical composition in combination with a pharmaceutically acceptable carrier, diluent or excipient. The compound of the invention, while effective itself, is typically formulated and administered in the form of their pharmaceutically acceptable salts as these forms are typically more stable, more easily crystallised and have increased solubility.

The compound is, however, typically used in the form of pharmaceutical compositions which are formulated depending on the desired mode of administration. As such in some embodiments the present invention provides a pharmaceutical composition including a compound of the invention and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compound of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compound of the invention may be used in a combination therapy. When this is done the compound is typically administered in combination with each other. Thus the compound of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compound can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

Synthesis of the Compound of the Invention 5-(9-isopropyl-8-methyl-2-morpholin-4-yl-9H-purin-6-yl)-pyrimidin-2-ylamine was prepared from dichloropurine using a 5 step procedure depicted in scheme 1.

Scheme 1

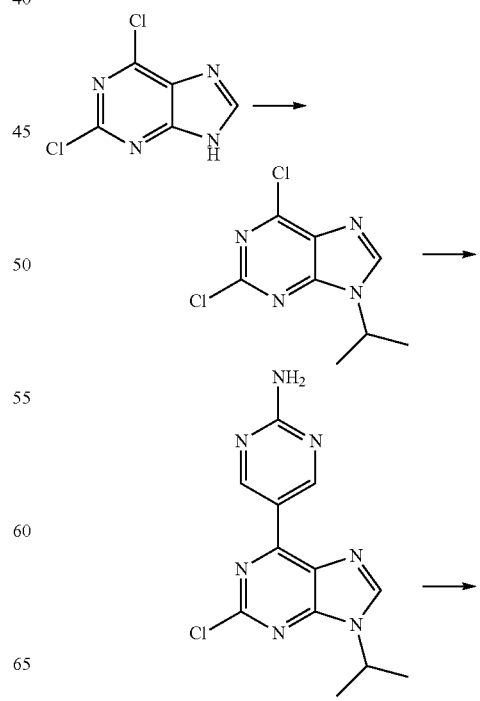

-continued

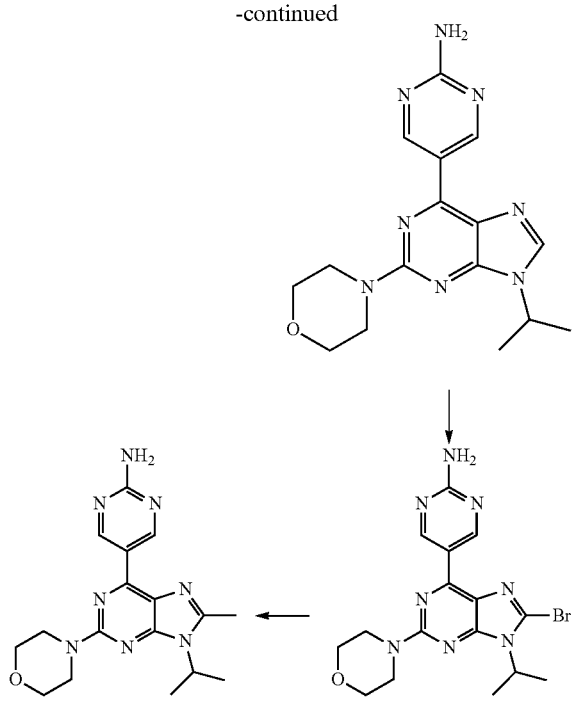

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60 F 254 plates (E Merck (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat, or by staining in an iodine chamber.

Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo.

Flash column chromatography [Still et al, J. Org. Chem., 43, 2923 (1978)] was conducted using E Merck-grade flash silica gel (47-61 mm) and a silica gel:crude material ratio of about 20:1 to 50:1, unless otherwise stated. Hydrogenolysis was done at the pressure indicated or at ambient pressure.

$^1$H NMR spectra were recorded on a Bruker instrument operating at 400 MHz, and $^{13}$C-NMR spectra was recorded operating at 100 MHz. NMR spectra were obtained as CDCl$_3$ solutions (reported in ppm), using chloroform as the reference standard (7.27 ppm and 77.00 ppm) or CD$_3$OD (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz. Mass spectra were obtained using LC/MS either in ESI or APCI. All melting points are uncorrected. All final products had greater than 90% purity (by HPLC at wavelengths of 220 nm and 254 nm).

The following synthetic examples are intended to illustrate one method of synthesising the compound of the invention and are not to be construed as being limitations thereto.

Example 1

Synthesis of the Compound of the Invention

Synthesis of 2,6-dichloro-9-isopropyl-9H-purine

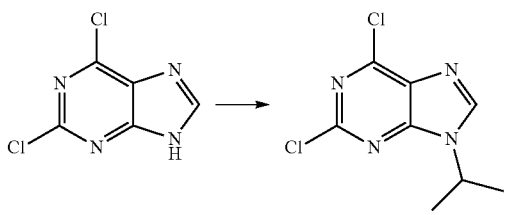

2,6-Dichloropurine (2 mmol), isopropanol (8 mmol) and triphenylphosphine (4 mmol) were taken up in 40 ml anhydrous tetrahydrofuran and diisoproplyazidodicarboxylate (4 mmol) was added drop wise at room temperature over a period of 30 min. The reaction mixture was then stirred at room temperature for a further 24 h. The reaction was periodically monitored by TLC or LC-MS. The reaction mixture was poured in to a beaker containing ice-cold water. Extraction of the aqueous layer, using 3×100 ml portions of ethyl acetate, afforded the crude product. This was purified by chromatography on a silica gel column (10-80% ethyl acetate in petroleum ether, gradient elution), to give 2,6-dichloro-9-isopropyl-9H-purine in a yield of 77%.

Synthesis of 5-(2-chloro-9-isopropyl-9H-purin-6-yl)-pyrimidin-2-ylamine

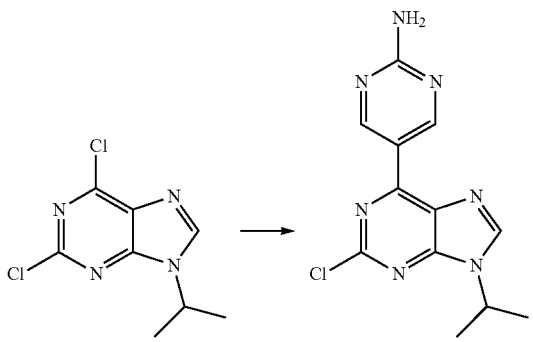 [SMILES: CC(C)n1cnc2c(Cl)nc(Cl)nc21 ; CC(C)n1cnc2c(-c3cnc(N)nc3)nc(Cl)nc21]

To a solution of 2,6-dichloro-9-isopropyl-9H-purine (5.21 mmol), 5-(4,4,5,5-tetramethyl-[1,3,2]dioxaborolan-2- ylamine (5.21 mmol) and 1,1'-bis(diphenylphosphino) ferrocene palladium (II) chloride complexed with dichloromethane (0.26 mmol) in peroxide free dioxane (40 ml) was added a 2M aqueous solution of sodium carbonate (15.6 mmol). The resulting mixture was degassed and purged with nitrogen. This reaction mixture was then stirred while being heated on an oil bath maintained at 80° C. for 3 h. The reaction was monitored by LC-MS for the disappearance of the starting purine.

The reaction mixture was cooled to room temperature and the solvents removed under reduced pressure. The residue was taken up in a mixture of ethyl acetate and water. The organic phase was separated and the aqueous layer further extracted with 3×100 ml portions of ethyl acetate. The organics were dried over sodium sulfate and the solvents removed under vacuum to give 5-(2-chloro-9-isopropyl-9H-purin-6-yl)-pyrimidin-2-ylamine in 55% yield.

Synthesis of 5-(9-isopropyl-2-morpholin-4-yl-9H-purin-6-yl)-pyrimidin-2-ylamine

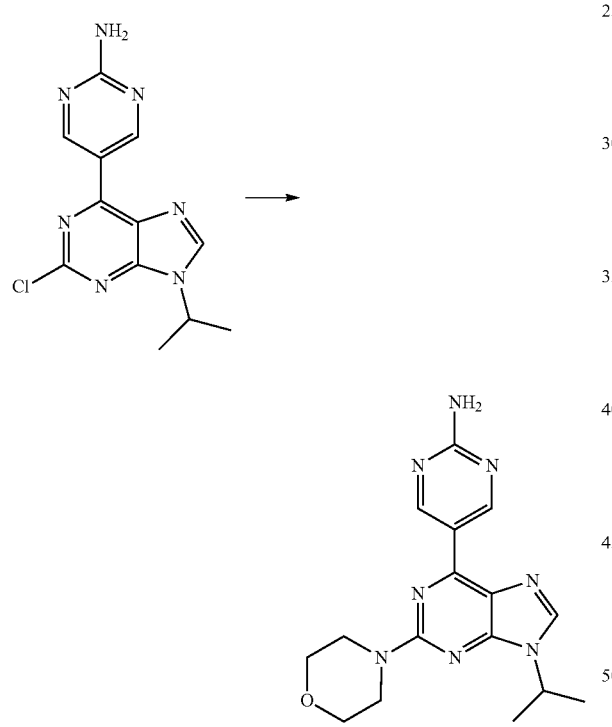

To a solution of 5-(2-chloro-9-isopropyl-9H-purin-6-yl)-pyrimidin-2-ylamine (2.84 mmol) in dimethyl acetamide (18 ml) was added morpholine (2.84 mmol). The reaction mixture was stirred while being heated on an oil bath maintained at 94° C. for 12 h. The reaction was monitored for the absence of starting material by LC-MS. The crude material was directly loaded onto a preparative HPLC column and purified by chromatography to give 5-(9-isopropyl-2-morpholin-4-yl-9H-purin-6-yl)-pyrimidin-2-ylamine in a yield of 58%. $^1$H NMR, DMSO-d6: 9.53 (s, 2H), 8.32 (s, 1H), 7.30 (bs, 2H), 4.72 (m, 1H), 3.78 (m, 4H), 3.73 (m, 4H), 1.55 (d, 6H). m/z: 341.17 [MH]$^+$.

Synthesis of 5-(8-bromo-9-isopropyl-2-morpholin-4-yl-9H-purin-6-yl)-pyrimidin-2-ylamine

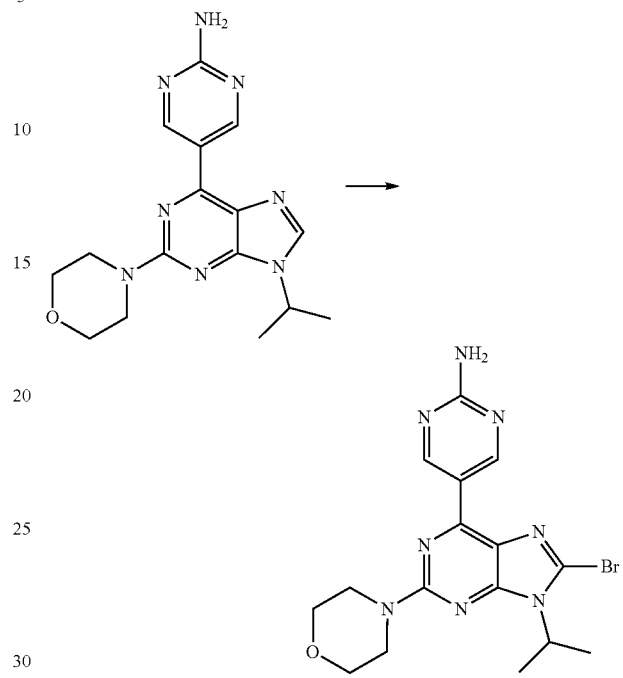

To a solution of 5-(9-isopropyl-2-morpholin-4-yl-9H-purin-6-yl)-pyrimidin-2-ylamine, (1.03 g, 3.03 mmol) in 15 ml of chloroform, was added slowly NBS (594 mg, 3.34 mmol) at a temperature of 5° C. The reaction was continued for 2 h at this temperature. After simple work-up, the product 5-(8-bromo-9-isopropyl-2-morpholin-4-yl-9H-purin-6-yl)-pyrimidin-2-ylamine was purified by flash column (solvent system: 50% ethyl acetate in hexane) to deliver 5-(8-bromo-9-isopropyl-2-morpholin-4-yl-9H-purin-6-yl)-pyrimidin-2-ylamine in a yield of 52% (660 mg). $^1$H NMR, MeOD: 9.67 (s, 2H), 4.90 (m, 1H), 3.89 (m, 4H), 3.82 (s, 4H), 1.72 (d, 6H). m/z: 419.31, 421.07 [MH]$^+$.

Synthesis of 5-(9-isopropyl-8-methyl-2-morpholin-4-yl-9H-purin-6-yl)-pyrimidin-2-ylamine

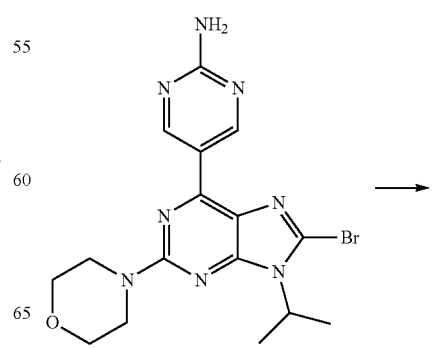

-continued

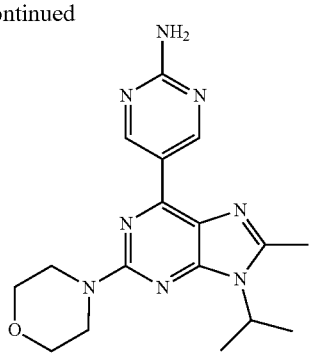

To a solution of 5-(8-bromo-9-isopropyl-2-morpholin-4-yl-9H-purin-6-yl)-pyrimidin-2-ylamine, (30 mg, 0.072 mmol) and Pd(dppf)Cl$_2$, (3 mg, 5% mmol) in 3 ml of anhydrous dioxane, was added slowly dimethyl zinc (210 μl, 1.0 M in heptane solution) in a sealed tube. The mixture was heated to about 65° C. MeOH was added drop wise and the solvents removed in vacuo. EtOAc was added to the residue and the resulting solution washed with 1 M HCl, water, brine and then dried over Na$_2$SO$_4$. The solvent was removed and the crude mixture was subjected to flash chromatography on silica gel to obtain 5-(9-isopropyl-8-methyl-2-morpholin-4-yl-9H-purin-6-yl)-pyrimidin-2-ylamine 8 mg in a yield of 47%. $^1$H NMR, MeOD: 9.40 (s, 2H), 4.81 (m, 1H), 3.89 (m, 4H), 3.82 (s, 4H), 3.71 (s, 3H), 1.73 (d, 6H). m/z: 355.16 [MH]$^+$.

Example 2

Comparative Biological Testing

The compound of the invention was compared to a number of compounds synthesised and disclosed in PCT/SG2008/000379 on a number of biological parameters.
The parameters tested were:
Activity in an mTOR assay;
Activity in a PI3K assay;
Solubility assay
Human microsomal stability assay
Details of the methodology of each of these tests are detailed below:
mTOR Assay
Truncated mTOR kinase and His-tagged 4eBP1 were produced in-house. [γ$^{33}$P]-ATP was purchased from Amersham (GE Healthcare). All chemicals, unless otherwise stated, were from Sigma-Aldrich.
Phosphorylation assays were initially performed in a final volume of 20 μL in 384-well polypropylene plate (Greiner). Compounds were typically tested over the range from 100 μM to 0.006 μM, in 8 step dilutions, in duplicate. 10 μL/well of 2× Enzyme-Substrate solution (1.5 μg/mL mTOR, 40 μg/mL 4eBP1 in 1× assay buffer: 10 mM Hepes pH 7.5, 50 mM NaCl and 10 mM MnCl$_2$) were first added to the sample plate containing 1 μL/well of test compound in neat DMSO. The reaction was initiated by adding 10 μL/well of 20 μM ATP solution (final assay concentration 10 μM ATP and 0.4 μCi/well of [γ$^{33}$P]-ATP). After 1 hour incubation at room temperature, the reaction was terminated with 40 μL/well of 20 mM EDTA/1 mM ATP solution.
50 μL/well of the stopped reaction mix was then transferred to a 384-well MultiScreenHTS-PH filter plate (Millipore) pre-added with 50 μL/well of 1% phosphoric acid. The plate was washed 4 times with 120 μL/well of 0.5% phosphoric acid via vacuum filtration. Finally, 10 μL/well of Optiphase™ SuperMix liquid scintillation cocktail (Perkin Elmer) was added. After minimum 1 hour of incubation, counting was performed in a Wallac MicroBeta TriLux scintillation counter using coincidence counting mode with crosstalk correction. IC$_{50}$ is defined as the concentration of compound required for 50% of maximum possible inhibition of kinase enzyme activity.

PI3K Assay

Recombinant PI3K p110α/p85 was prepared in-house. Phosphatidylinositol (PtdIns), phosphotidylserine (PtdSer) and all other unspecified chemicals were purchased from Sigma-Aldrich. [γ$^{33}$P]ATP and Optiphase scintillant were obtained from Perkin Elmer.
Assays were performed in a final assay volume of 25 μL in 384-well Maxisorp plates (Nunc). Compounds were tested at 8 concentrations in 3-fold serial dilution, generally starting from 10 μM. Maxisorp plates were coated with 20 μL/well of a 1:1 mixture of PtdIns and PtdSer [0.1 mg/mL each dissolved in chloroform:ethanol (3:7)] and left overnight in a fume hood at room temperature (RT) to dry.
The enzyme reaction was created by pipetting 5 μL/well of compound (in 2.5% DMSO), 10 μL/well of enzyme (0.5 μg/mL p110α+1 μg/mL p85), and 10 μL/well of 5 μM ATP with 5 μCi/mL [γ$^{33}$P]ATP in assay buffer (final concentrations: 0.2 μg/mL p110α, 2 μM ATP, 0.05 μCi/well [γ$^{33}$P]ATP in 1× assay buffer: 100 mM Tris-HCl pH 7.0, 200 mM NaCl, 8 mM MgCl$_2$). The reaction was incubated for 1 hour at RT and terminated with 30 μL/well of 50 mM EDTA solution. The plate was then washed twice with TBS, dried, and added with 30 μL/well of scintillant before it was counted in a MicroBeta Trilux. IC$_{50}$ is defined as the concentration of compound required for 50% of maximum possible inhibition of kinase enzyme activity.

Microsomal Stability Assay

Compound stability is initially assessed in vitro using a high throughput format in 96 well plates (Whatman) involving incubation with human liver microsomes (HLM). Verapamil, purchased from Sigma-Aldrich, is used as a reference standard in the assay. HLM are purchased from Xeno Tech (20 mg/mL in 250 mM sucrose solution). A 100 mM stock solution of potassium phosphate buffer is pre-prepared by combining 80 mL of 1M K$_2$HPO$_4$ and 20 mL of 1 M KH$_2$PO$_4$ in 900 mL of water (pH adjusted to 7.4 using diluted HCl) and stored at room temperature. K$_2$HPO$_4$.3H$_2$0 and KH$_2$PO$_4$ are obtained from Sigma Aldrich and the NADPH Regeneration System Solutions A and B from Gentest. The stop solution used to quench the reaction is a pre-prepared mixture of acetonitrile and DMSO (80:20) and is stored at 4° C. All solvents used are HPLC grade and the water used during the stock solution preparation and during LC-MS analysis is deionised using a Milli-Q system.
2.5 μL of a 10 mM stock solution of the test compound in DMSO is diluted 200 times by mixing with 500 μL of a 50 mM potassium phosphate buffer (pH 7.4, prepared by dilution of the 100 mM stock buffer solution with water) to give 500 μL of a 50 μM solution. 8 μL of the compound mix is then added to 72 μL of a pre-prepared incubation mix made up of water (2250 μL), 100 mM potassium phosphate buffer (2900 μL), NADPH Regeneration System Solution B (58 μL), NADPH Regeneration System Solution A (290 μL) and HLM (250 μL). The resulting reaction mixture (final compound concentration of 5 μM) is then incubated at 37° C. in a B. Braun Certomat H incubator after which a 50 μL aliquot is dispensed to a well on a separate plate well containing 100 μL of Stop solution. After centrifugation at 4° C. for 15 min at 2000 rpm a 100 μL sample of the resulting supernatant is transferred to an LC-MS plate for analysis. Each test compound is sampled multiple times and incubated for a series of time points (5, 15, 30, 45 and 60 min). Remaining compound concentration is determined by LC-MS (ABI Qtrap 3200) and comparison to a reference solution of known concentration. Stability is then expressed as a half-life in minutes (t½).

High Throughput Solubility Assay

Compound solubility is determined in a high-throughput kinetic solubility profiling method using a 96-well format. Compound solubility is assessed using a UV/Visible Microplate Spectrophotometer (Molecular Devices SpectraMax Plus384). Vorinostat (SAHA) and Nicardipine, purchased from Sigma, are used as reference standards.

Compounds in DMSO are diluted with phosphate buffer (Sigma) at a final concentration of 250 µM (5 µL of a 10 mM stock solution in 195 µL phosphate buffer pH 7) and thoroughly mixed. The mixture is then shaken at 600 rpm for 1.5 h and allowed to stand at room temperature for 2 h. The plate is then centrifuged at 1500 g for 15 min. The resulting supernatant (80 µL) is transferred to the UV-analysis plate and diluted with DMSO (20 µL). The samples are quantified using calibration stocks of the respective compound made in phosphate buffer/DMSO (80:20).

The compounds tested were as follows:

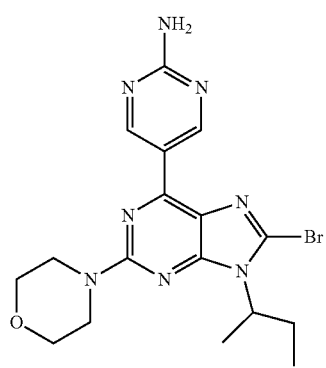

Compound A

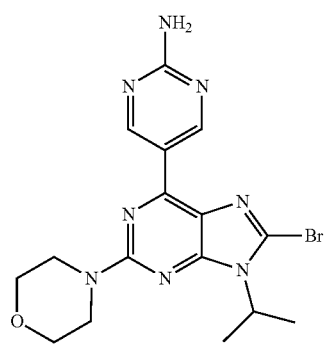

Compound B

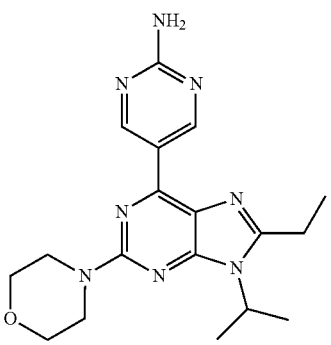

Compound C

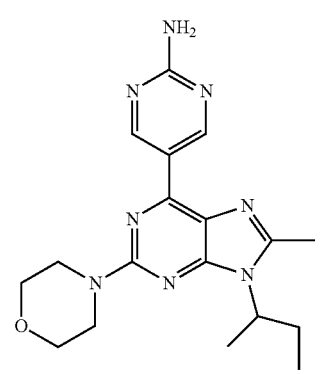

Compound D

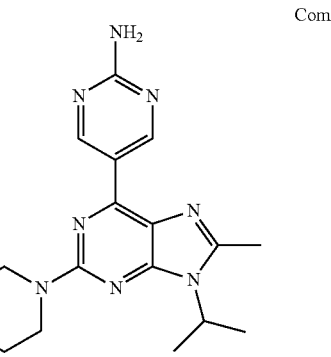

Compound of the Invention

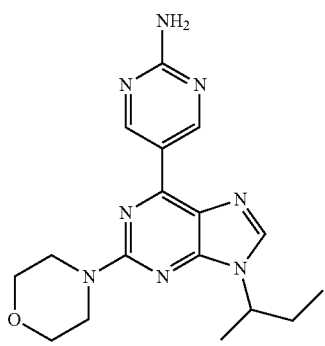

Compound E

The results of the biological testing are summarised in table 1.

TABLE 1

|  | Cmpd A | Cmpd B | Cmpd C | Cmpd D | Cmpd E | Cmpd of the invention |
| --- | --- | --- | --- | --- | --- | --- |
| mTOR | 21 nM | 16 nM | 27 nM | 40 nM | 122 nM | 36 nM |
| PI3K | 43 nM | 17 nM | 16 nM | 15 nM | 18 nM | 11 nM |
| Solubility | 44 µM | 18 µM | >250 µM | >250 µM | 35 µM | 178 µM |
| T½ HLM | >60 min | >60 min | 36 min | 26 min | >60 min | >60 min |

As can be seen whilst all compounds had some degree of activity the compound of the invention had activity against both the enzymes of interest comparable to the activity of all the comparator compounds except compound E which had significantly lower activity against mTOR. As such all the compounds were potential drug candidates although compound E was somewhat less active against mTOR.

Not all the compounds tested displayed acceptable solubility characteristics, however. For example the low solubility results for compounds A, B and E meant that these compounds would not make good drug candidates. Their low solubilities make them difficult to formulate effectively in physiologically acceptable carriers hence reducing the likelihood that they would have good oral pharmacokinetics in humans. In contrast the solubility of compounds C, D and the compound of the invention were acceptable for drug candidate compounds.

In relation to in vitro metabolic stability, however, the results were significantly different. In these tests compounds A, B, E and the compound of the invention had acceptable stability in human liver microsome studies. This suggests that if these compounds could be successfully administered then they would be sufficiently stable to achieve the desired physiological effect in the patient. Moreover of the compounds which exhibit both good mTOR/PI3K inhibitory activity and good solubility (C,D and the compound of the invention), the only one with acceptable metabolic stability is the compound of the invention.

All the compounds A-E and the compound of the invention show good activity in these assays but the compound of the invention is one of the strongest due to its combination of potent target inhibition activity, good aqueous solubility and good metabolic stability.

In summary the biological results achieved for the compounds tested in the biological studies conducted above suggest that notwithstanding the apparently close similarity of the compound of the invention with a number of the comparator test compounds the compound of the invention is the only one that demonstrates the required combination of activity, sufficient aqueous solubility and metabolic stability to suggest that the compound has application as a drug moiety. These studies therefore demonstrate the superiority of this compound as a drug candidate.

Example 3

Cell-Based Efficacy Biomarker Assays (pp70-S6KT389, pAktS473)

In order to further demonstrate the efficacy of the compound of the invention two cell based biomarker assays were conducted on the compound of the invention. The methodology was as follows:
AlphaScreen® SureFire p-Akt (Ser 473) 384 Kit (TGR, Cat. No.: TGRAS500),
AlphaScreen® SureFire phospho-p70 S6 kinase (Thr 389) 384 kit (TGR, Cat. No.:TGR70S500) and Proxiplate-384 Plus (Perkin Elmer, Cat. No.: 6008280) were purchased from Perkin Elmer. The human prostatic carcinoma cell line (PC-3) was purchased from ATCC. All chemicals, unless otherwise stated, were from Sigma-Aldrich.

On Day 1, 200 µl of a 2×105 cells/ml cell solution of PC3 cells were seeded into each well of a 96-well plate. Compounds were added 24 h after seeding and were typically tested over a range from 10 µM to 4.6 nM, in 8 step dilutions, in triplicate. The final concentration of DMSO during the 4 h incubation step at 37° C. was 0.1%. After the incubation step, the supernatant was removed, the cells were lysed with 1× Lysis buffer (provided by the AlphaScreen kit) and gently shaken for 10 min. 4 µl of the lysates and 5 µl of the Reaction Buffer plus Activation buffer mix containing AlphaScreen Acceptor beads were added into each 384-well (Ratio of Reaction Buffer:Activation Buffer:Acceptor Beads is 40:10:1) and gently shaken for 2 h (room temperature, dark). 2 µl of Dilution buffer containing AlphaScreen® Donor beads (Ratio of Dilution Buffer:Donor Beads is 20:1) were added into each well on a 384-plate, placed on a plate shaker for 1-2 mins and incubated at room temperature overnight.

A BMG Pherostar plate reader was used to read the 384-well plate using standard AlphaScreen settings (Measurement mode: Alphascreen; reading mode: Endpoint; optic mode: AlphaScreen 680 570; Position delay: 0.10 s; Excitation time: 0.30 s; Integration start: 0.34 s; integration time: 0.30 s; Gain: 3000).

$IC_{50}$ is defined as the molar concentration of a compound, which produces 50% of the maximum possible inhibition of kinase enzyme activity by this compound. The $IC_{50}$ of 5-(9-isopropyl-8-methyl-2-morpholin-4-yl-9H-purin-6-yl)-pyrimidin-2-ylamine for inhibition of of phosphorylation of p70-S6KT389 and pAktS473 was found to be 24 nM and 9 nM respectively.

The biomarker results demonstrate the efficacy of the compound of the invention in the inhibition of kinase enzyme activity.

What is claimed is:
1. A pharmaceutical composition comprising a compound of formula (I):

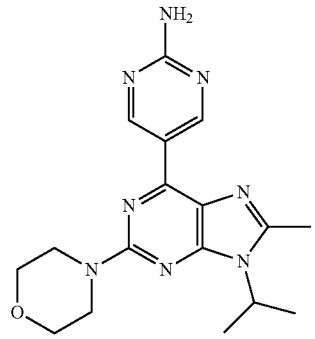

Formula (I)

or a pharmaceutically acceptable salt thereof, and a pharmaceutically acceptable diluent, excipient or carrier.

2. A method of inhibiting a protein kinase selected from the group consisting of a serine/threonine protein kinase or a fragment or a complex thereof or a functional equivalent thereof and a PI3 kinase or a fragment or a complex thereof or a functional equivalent thereof, the method including exposing the protein kinase or a fragment or complex thereof or a functional equivalent thereof and/or co-factor(s) thereof to an effective amount of a compound of formula (I):

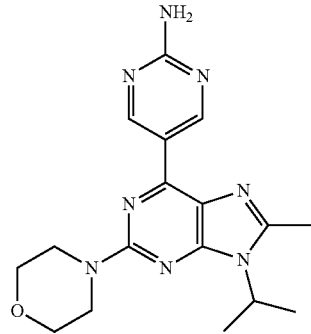

Formula (I)

or a pharmaceutically acceptable salt thereof, wherein the serine/threonine protein kinase or fragment or complex thereof is an mTOR protein kinase, or a fragment thereof, or a complex thereof or a functional equivalent thereof.

3. The method according to claim 2, wherein the protein kinase is an mTOR protein kinase, or a fragment thereof, or a complex thereof or a functional equivalent thereof.

4. The method according to claim 3, wherein the mTOR protein kinase or fragment or complex or functional equivalent thereof is selected from the group consisting of mTORC1 or a fragment or complex thereof or a functional equivalent thereof and mTORC2 or a fragment or complex thereof or a functional equivalent thereof.

5. The method according to claim 2 wherein the protein kinase is a PI3K kinase or a fragment thereof or a complex thereof or a functional equivalent thereof.

6. The method according to claim 5 wherein the PI3 kinase or a fragment thereof or a complex thereof or a functional equivalent thereof, is a class I PI3K or a fragment thereof or a complex thereof or a functional equivalent thereof.

\* \* \* \* \*